3/24/81    XR    4,257,271

United States Patent [19]

Glenn

[11] 4,257,271
[45] Mar. 24, 1981

[54] SELECTABLE DELAY SYSTEM

[75] Inventor: William E. Glenn, Fort Lauderdale, Fla.

[73] Assignee: New York Institute of Technology, Old Westbury, N.Y.

[21] Appl. No.: 429

[22] Filed: Jan. 2, 1979

[51] Int. Cl.³ ............................................ G01N 29/00
[52] U.S. Cl. ...................................... 73/626; 128/660
[58] Field of Search ................. 73/609, 620, 625, 626, 73/628; 128/660; 340/1 R, 3 R; 333/165; 367/103, 105, 122, 123, 125, 138

[56] References Cited

U.S. PATENT DOCUMENTS

| 2,406,340 | 8/1946 | Batchelder | 367/125 |
|---|---|---|---|
| 3,166,731 | 1/1965 | Joy | 73/626 |
| 4,005,382 | 1/1977 | Beaver | 73/626 |
| 4,012,952 | 3/1977 | Dory | 73/626 |
| 4,019,169 | 4/1977 | Takamizawa | 73/626 |
| 4,116,229 | 9/1978 | Pering | 73/626 |
| 4,127,034 | 11/1978 | Lederman et al. | 73/626 |

Primary Examiner—Stephen A. Kreitman
Attorney, Agent, or Firm—Martin Novack

[57] ABSTRACT

A selectable delay system for coupling between a plurality of elements and an input/output terminal, the relative delays between the input/output terminal and the individual elements being selectable under operator control. A single delay line is employed to obtain up to three different effective delay configurations that can be used, for example, to obtain three different focuses in an ultrasonic imaging system.

8 Claims, 4 Drawing Figures

SELECTABLE DELAY SYSTEM

BACKGROUND OF THE INVENTION

This invention relates to variable delay techniques and, more particularly, to a selectable delay system. The subject matter of this invention is related to subject matter disclosed in my copending U.S. application Ser. No. 000,430 entitled "Variable Delay System", filed of even date herewith and assigned to the same assignee as the present application. The invention is especially useful in ultrasonic imaging systems.

In recent years ultrasonic techniques have become more prevalent in clinical diagnosis. Such techniques have been utilized for some time in the field of obstetrics, neurology and cardiology, and are becoming increasingly important in the visualization of subcutaneous blood vessels including imaging of smaller blood vessels.

Various fundamental factors have given rise to the increased use of ultrasonic techniques. Ultrasound differs from other forms of radiation in its interaction with living systems in that it has the nature of a mechanical wave. Accordingly, information is available from its use which is of a different nature than that obtained by other methods and it is found to be complementary to other diagnostic methods, such as those employing X-rays. Also, the risk of tissue damage using ultrasound appears to be much less than the apparent risk associated with ionizing radiations such as X-rays.

The majority of diagnostic techniques using ultrasound are based on the pulse-echo method wherein pulses of ultrasonic energy are periodically generated by a suitable piezoelectric transducer such as a lead zirconate-titanate ceramic. Each short pulse of ultrasonic energy is focused to a narrow beam which is transmitted into the patient's body wherein it eventually encounters interfaces between various different structures of the body. When there is a characteristic impedence mismatch at an interface, a portion of the ultrasonic energy is reflected at the boundary back toward the transducer. After generation of the pulse, the transducer operates in a "listening" mode wherein it converts received reflected energy or "echoes" from the body back into electrical signals. The time of arrival of these echoes depends on the ranges of the interfaces encountered and the propagation velocity of the ultrasound. Also, the amplitude of the echo is indicative of the reflection properties of the interface and, accordingly, of the nature of the characteristic structures forming the interface.

There are various ways in which the information in the received echoes can be usefully presented. In one common technique, the electrical signals representative of detected echoes are amplified and applied to the vertical deflection plates of a cathode ray display. The output of a time-base generator is applied to the horizontal deflection plates. Continuous repetition of the pulse/echo process in synchronism with the time-base signals produces a continuous display, called an "A-scan", in which time is proportional to range, and deflections in the vertical direction represent the presence of interfaces. The height of these vertical deflections is representative of echo strength.

Another common form of display is the so-called "B-scan" wherein the echo information is of a form more similar to conventional television display; i.e., the received echo signals are utilized to modulate the brightness of the display at each point scanned. This type of display is found especially useful when the ultrasonic energy is scanned transverse the body so that individual "ranging" information yields individual scanlines on the display, and successive transverse positions are utilized to obtain successive scanlines on the display. The technique yields a cross-sectional picture in the plane of the scan, and the resultant display can be viewed directly or recorded photographically or on magnetic tape. The transverse scan of the beam may be achieved by a reflector which is scanned mechanically over a desired angle.

Two types of focusing techniques are most prevalent in ultrasonic imaging equipment; i.e., fixed focus and dynamic focus. In a fixed focusing technique, the returning echoes are assumed to originate from a particulate range in the body being imaged. Based on this assumption, appropriate delays are imparted to the different portions of the returning ultrasound beam so that all portions of the beam arriving at the transducer from the particular range can be added approximately in phase. The focusing may be achieved, for example, by providing a focusing lens (as described in the U.S. Pat. No. 3,958,559), by providing a segmented transducer in conjunction with appropriate fixed delays, or by combinations of these or other techniques.

Dynamic focusing techniques typically utilize a segmented transducer and the signals received at the transducer segments are summed through appropriate variable delays to obtain different effective foci as a function of time. As the investigating beam moves deeper into the body, the variable delays are varied appropriately to move the effective focus deeper into the body.

Fixed focus systems are advantageous in that they are less complex and less expensive than their dynamically focused counterparts. However, when it is desired to have an equipment which can operate over a substantial range of depth in a body, a fixed focus system may be inadequate. However, in such cases a full dynamic focusing capability may not be required and could involve undue complexity and expense.

It is one of the objects of the present invention to provide an ultrasonic imaging apparatus which includes a selectable focus having performance advantages as compared to fixed focus techniques, but which is less complex than prior art dynamic focusing techniques.

SUMMARY OF THE INVENTION

The present invention is directed to a selectable delay system for coupling between a plurality of elements and an input/output (i.e., input and/or output) terminal, the relative delays between the input/output terminal and the individual elements being selectable under operator control. A single delay line is employed to obtain up to three different effective delay configurations that can be used, for example, to obtain three different focuses in an ultrasonic imaging system.

In accordance with the invention, there is provided a delay line having multiple delay stages in a serially connected string. Means are provided for coupling the delay stages to respective ones of the plurality of elements. A switching means is provided for coupling, under operator control, either one end or the other end of the delay line to the input/output terminal. In the preferred form of the invention, the switching means further comprises means for coupling, without relative delay therebetween, each of the elements to the input- /output terminal. In this embodiment, the means for coupling without relative delay preferably comprises a portion of the switching means coupled between the common connection of the delay line and the input/output terminal. Also, in the preferred embodiment, means operative in conjunction with the switching means are provided for coupling a terminating impedance at the end of the delay line which is not coupled to the input/output terminal.

The present invention is particularly, although not necessarily, applicable to an apparatus for imaging a body by transmitting ultrasound energy into the body. Such an apparatus typically includes a pulser/receiver and a transducer having a number of segments for transmitting ultrasound energy (from the pulser/receiver) into the body and for converting ultrasound reflected from the body into electrical signals. These electrical signals are coupled back to the pulser/receiver and then processed to obtain an image suitable for display. In an application of the present invention, the novel selectable delay system hereof is coupled between the pulser/receiver and the segments of the transducer.

Further features and advantages of the invention will become more readily apparent from the following detailed description when taken in conjunction with the accompanying drawings.

DESCRIPTION OF THE PREFERRED EMBODIMENT

Figure 1:
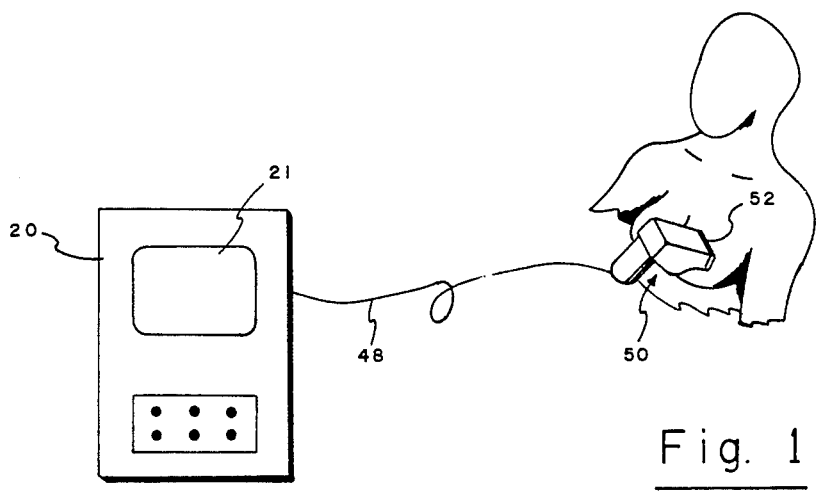
FIG. 1 illustrates the operation of an imaging apparatus which employs the improvements of the invention.

Referring to FIG. 1, there is shown an illustration of a scanning apparatus which employs the improvements of the invention. A console 20 is provided with a display 21 which may typically be a cathode ray tube television-type display, and a suitable control panel. A video tape recorder or suitable photographic means may also be included in the console to effect ultimate display of images. The console will typically house power supplies and portions of the timing and processing circuitry of the system to be described. A portable scanning module or probe 50 is coupled to the console by a cable 48. In the present embodiment the probe has a generally cylindrical handle and a scanning window 51 near one end. During operation of the apparatus, the probe 50 is handheld to position the scanning window over a part of the body to be imaged. For example, in FIG. 1 the probe is positioned such that a cross section of the breast will be obtained. Imaging of other portions of the body is readily attained by moving the probe to the desired position and orientation, the relative orientation of the scanning window determining the angle of the cross section taken.

Figure 2:
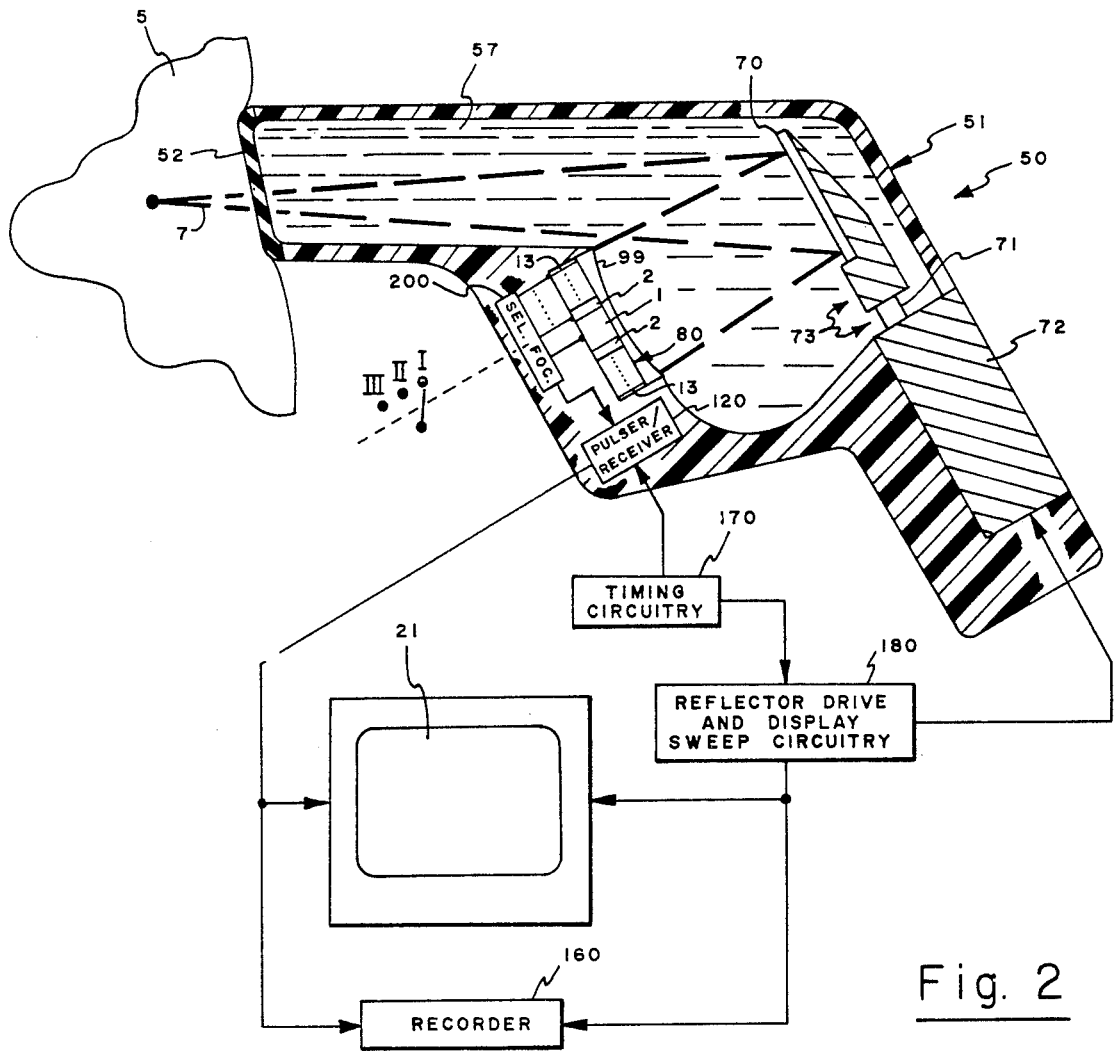
FIG. 2 is a schematic diagram, partially in block form, of an apparatus which employs the improvements of the invention.

Referring to FIG. 2, there is shown a cross-sectional view of a portion of the scanning module or probe 50 along with diagrams of portions of the circuitry therein and in console 20 used in conjunction therewith. An enclosure 51, which may be formed of a sturdy plastic, has scanning window 52 at the front end thereof. The enclosure 51 is filled with a suitable fluid 57, for example water. The scanning window 52 is relatively flat and may be formed, for example, of polystyrene or nylon. A reflective scanner 70, which is flat in the illustration but which may be curved to provide focusing if desired, is positioned at the approximate rear of the enclosure 51 and substantially faces the window 52. The scanner 70 is mounted on a shaft 71 which passes through a suitable seal and is connected to an electric motor 72 which is mounted in a recess in enclosure 51 and is driven to provide the desired oscillatory motion of scanner 70, as depicted by curved two-headed arrow 73.

An ultrasonic transducer 80, which may have an associated focusing lens 99, is mounted in a compartment 59 of enclosure 51. The transducer is mounted relatively frontwardly of reflective scanner 70 in the module 50 with the ultrasound-emitting face of the transducer generally facing rearwardly in the module 50 and being directed toward the reflective scanner 70. As described in my copending U.S. application Ser. No. 890,378, assigned to the same assignee as the present application, the transducer 80 is positioned such that the ultrasound beam which it emits is reflected by the scanner 70 to double back past transducer 80 before passing through the window 52. The scanner preferably has a reflective surface formed of a material which results in a relatively small critical angle so that the beam impinging almost directly on the reflector surface will not pass through the reflector. The described arrangement makes efficient use of the volume of fluid 57 in the module 50 since the beam 7 is effectively "doubling back" past the transducer and experiencing a relatively large travel distance through a relatively small volume of water.

The transducer 80 is divided into a plurality of segments, typically a central circular segment surrounded by concentric annular segments. However, as described in my copending U.S. application Ser. No. 890,377, assigned to the same assignee as the present application, the transducer may alternatively have a generally elliptical shape. Also, for other applications of the invention, different transducer configurations, including linear arrays, can be employed. In FIG. 2 only some of thirteen segments designated 1, 2 . . . 13 are shown for ease in illustration, although it will be understood that the principles of the invention are readily applicable regardless of the number of segments employed.

The segments of transducer 80 are coupled to a pulser/receiver 120 via novel selectable focusing circuitry 200 to be described. The pulser/receiver is also coupled to display 21 and recorder 160, and the pulser/receiver 120 receives timing signals from timing circuitry 170. Suitable pulser/receiver and timing circuitry are well known in the art and are not the subject of this invention. The display 21 and recorder 160, may be any suitable recording or memory means such as a video tape recorder. If desired, gain control circuitry may be provided and may include interactive gain compensation, which is described in detail in U.S. Pat. No. 4,043,181. Interactive gain compensation circuitry compensates the amplitude of later arriving signals for attenuation experienced during passage through body tissue and losses due to prior reflections. The timing circuitry 170 generates timing signals which synchronize operation of the system; the timing signals being coupled to the circuitry 120 to alternately energize the transmitting and receiving modes, and also to reflector drive and display sweep circuitry 180, which generates the signals that control the oscillation of scanner 70 and the vertical and horizontal sweep signal for the display 21 and recorder 160.

In broad terms, operation of the system is as follows: Upon command from a trigger signal from the timing circuitry 170, the pulser 120 generates pulses which excite the segments of transducer 80 via selectable focusing circuitry 200. The ultrasound energy is reflected off of the surface of scanner 70 and into the body 5, as represented in FIG. 2, the dashed line depicting the beam outline. When the ultrasound beam has been transmitted toward the body, the timing circuitry initiates the "receive" or "listen" mode of pulser/receiver 120. Now, the transducer 80 serves to convert ultrasound energy, which is in the form of echoes reflected from the body and back off the scanner 70, into electrical signals. These signals are coupled, via circuitry 200 and 120, to the display 21. For a "B-scan" display, a sweep over a range of depths (which naturally results from the transmitted energy reflecting off different interfaces at successive depths in the body) corresponds to a horizontal scan line of the display. The second dimension of the desired cross-sectional image is obtained by a slower mechanical scan of scanner 70, the mechanical scanning range being illustrated by the double-headed arrow 73. Operation as described in this paragraph is generally in accordance with known techniques, novel aspects of the present invention residing, inter alia, in the selectable focusing circuitry 200 to be described.

Figure 3:
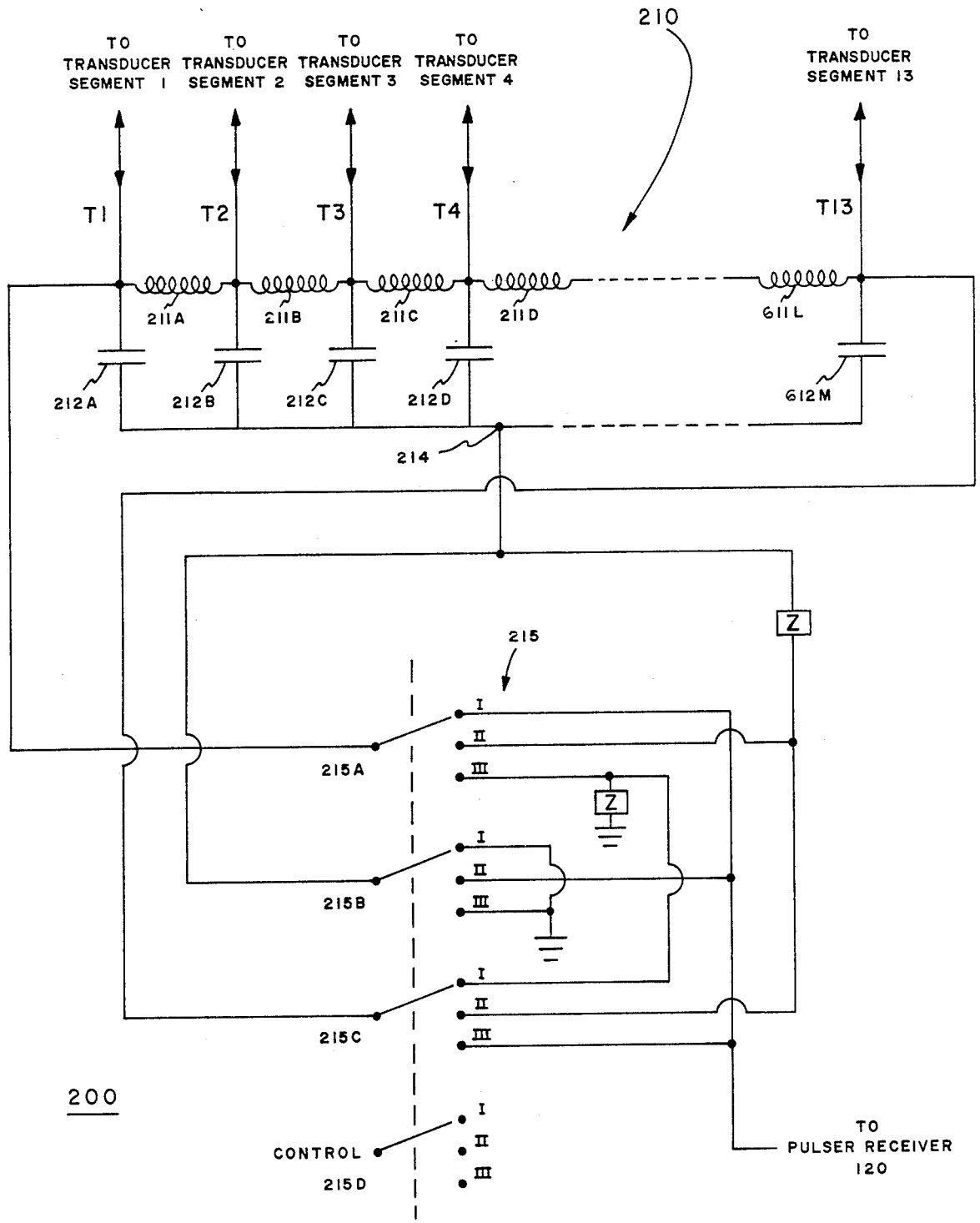
FIG. 3 is a schematic diagram of a selectable focusing system in accordance with an embodiment of the invention.

Referring to FIG. 3, there is shown an embodiment of the selectable focus circuitry 200 in accordance with the invention. A delay line 210 is provided, and includes delay stages in a conventional serially connected string. In the present embodiment, the delay stages comprise respective inductors 211A, 211B ... 211L (twelve in all) and capacitors 212A, 212B ... 212M (thirteen in all). The delay line 210 has taps designated T1, T2, ... T13 coupled to one plate of the respective capacitors 212A, 212B ... 212M and the inductors 212A, 212B ... 212L are coupled between adjacent taps. The other plate of each capacitor is coupled to a terminal 214 generally known as the "common connection" of the delay line. The taps T1, T2 ... T13 of delay line 210 are also respectively coupled to the ordered segments 1, 2 ... 13 of transducer 80. In particular, tap T1 is coupled to segment 1, tap T2 is coupled to segment 2, and so on.

A switch 215 has three three-position sections, 215A, 215B, and 215C under common control (designated 215D). A wiper of switch section 215A is coupled to the tap T1 defining one end of delay line 210. A wiper of switch section 215C is coupled to the tap T13 defining the other end of delay line 210. Also, a wiper of switch section 215B is coupled to the common connection 214 of delay line 210. Position I of switch section 215A, position II of switch section 215B, and position III of switch section 215C are all coupled to the pulser/receiver 120 (FIG. 2). Position III of switch section 215A and position I of switch section 215C are coupled to ground reference potential via an impedance Z which is preferably the characteristic impedance of delay line 210. Also, position II of switch section 215A and position II of switch section 215C are coupled to the common connection 214 via impedance Z. Positions I and III of switch section 215B are coupled to ground reference potential.

Figure 4:
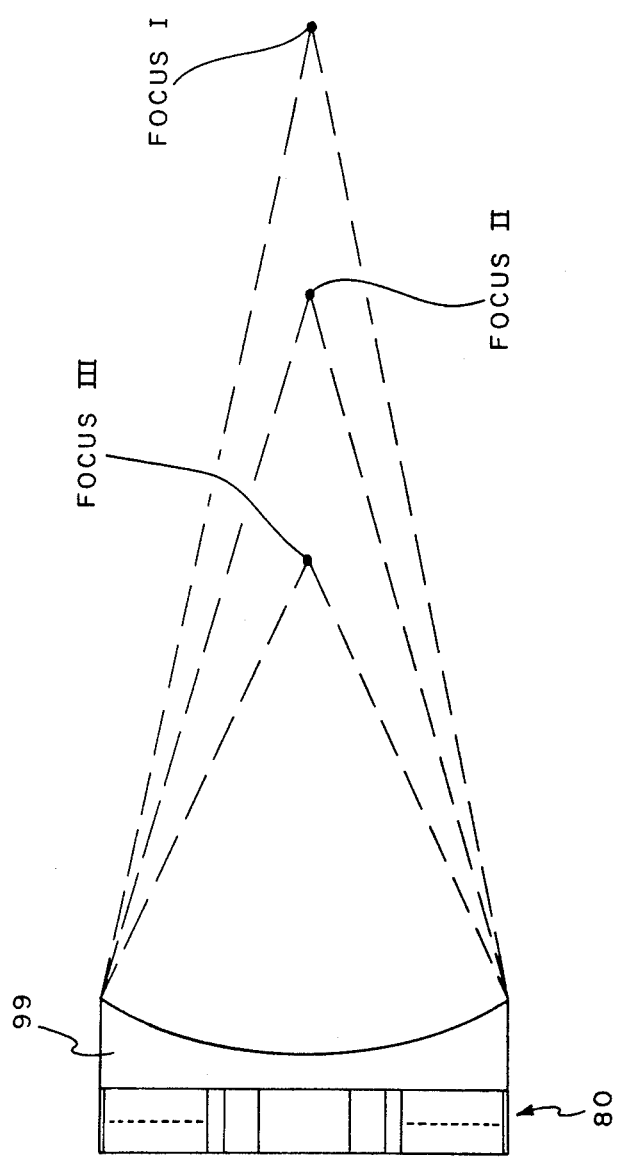
FIG. 4 is a diagram which illustrates the different focuses which can be obtained using the system of the invention.

In operation, the three switch positions, I, II and III are respectively used for a "far" focus, a "central" (or geometric) focus, and a "near" focus. In switch position II, switch section 215B is operative to couple the common connection 214 of the delay line to the pulser/receiver 120 and the switch sections 215A and 215C are each coupled through the impedance Z to the delay line common. In this manner, the pulser/receiver is coupled to each of the transducer segments without relative delay as between the different segments, and the ends of the delay line 210 are terminated with the characteristic impedance of the delay line. Accordingly, at switch position II, the system is focused at its geometrical focus, as determined by lens 99 (FIG. 2) and as illustrated in the diagram of FIG. 4 by "focus II".

When the switch is in position I the end of delay line 210 defined by tap T1 is coupled to the pulser/receiver via switch section 215A. In this position, the switch section 215B (i.e., delay line end T13) is coupled to ground reference potential and the switch section 215C (i.e. delay line common 214) is coupled to ground reference potential via impedance Z. Accordingly, in this switch position, the delays associated with transducer segments 1, 2 ... 13 are successively greater for the higher numbered segments. This can be readily understood by noting that the transducer segment 13 is coupled to the pulser/receiver via the full string of delay stages, transducer segment 1 is coupled to the pulser/receiver via no delay stages, and the intermediate segments of the transducer are coupled to the pulser/receiver via successively greater delays for the higher numbered segments. This results in the beam focus being at a "far" focal point ("focus I" of FIG. 4).

The opposite situation of the one just described is evident when the switch 215 is in position III. In this case, the T13 end of delay line 210 is coupled to pulser/receiver 120 via switch section 215C. The other end (T1) of delay line 120 is coupled to ground reference potential via characteristic impedance Z (switch section 215A) and the common connection 214 of the delay line is coupled to ground reference potential (switch section 215B). In this switch position successively greater delays are associated with lower numbered transducer segments; i.e., segment 1 experiences the greatest delay and segment 13 the least delay. The result is a focal point which is closer to the transducer than in the case of the geometrical focus; i.e., a "near" focal point ("focus III" of FIG. 4).

When the operator selects a particular switch position using control section 215D, the transmitted beam is directed toward the selected focus by employment of the selected group of delays, and the same delays are utilized during receiving. However, it will be understood that, if desired, a system can be configured such that the selected focusing is implemented during only transmitting or only receiving, with direct coupling to the pulser/receiver being utilized during the other mode of operation. The control 215D may be located in the console 20 and the sections A, B and C of the switch may, in such case, be under relay control.

It will be understood that the switch position associated with the central (or "geometric") focus could alternatively be operative to combine the signals from all transducer segments and couple them to the pulser/receiver while bypassing the delay line. Such an implementation may have some advantage in that it avoids coupling the signals through components of the delay line, but it has an attendant disadvantage in that a number of additional switches (one for each transducer segment) would be necessary.

The invention has been described with reference a particular embodiment, but variations within the spirit and scope of the invention will occur to those skilled in the art. For example, use of a lens (or other additional focusing such as a curved transducer or fixed delays) is not necessarily required. Also, it will be understood that the selectable delay system hereof can be used for other purposes, for example, selectable "steering" of an ultrasound beam to different discrete positions. Finally, it will be understood that only two of the three selectable delay modes can be utilized, if desired.

I claim:

1. A selectable delay system for coupling between a plurality of elements and an input/output terminal, the relative delays between the input/output terminal and the individual elements being selectable under operator control, comprising:
   a delay line having multiple fixed delay stages in a serially connected string;
   means for coupling said delay stages to respective ones of said elements; and
   switching means for coupling, under operator control either one end of said delay line, or the other end of said delay line, or the common connection of said delay line, to said input/output terminal.

2. The system as defined by claim 1 wherein said switching means is operative, when an end of said delay line is coupled to said input/output terminal, to couple the other end of said delay line to a ground reference via a terminating impedance and to couple said common connection of said delay line to a ground reference, and said switching means is further operative, when said common connection of said delay line is coupled to said input/output terminal, to couple both ends of said delay line to said ground reference via a terminating impedance.

3. Apparatus for imaging a body, comprising:
   a pulser/receiver;
   a transducer, having a number of segments, for transmitting ultrasound energy into said body and for converting ultrasound reflected from said body into electrical signals;
   a delay line having multiple fixed delay stages in a serially connected string;
   means for coupling said delay stages to respective ones of said segments;
   switching means for coupling, under operator control, either one end of said delay line, or the other end of said delay line, or the common connection of said delay line, to said pulser/receiver; and
   means coupled to said pulser/receiver for displaying an image of said body.

4. Apparatus as defined by claim 3 wherein said switching means is operative, when an end of said delay line is coupled to said pulser/receiver, to couple the other end of said delay line to a ground reference via a terminating impedance and to couple said common connection of said delay line to said ground reference, and said switching means is further operative, when said common connection of said delay line is coupled to said pulser/receiver, to couple both ends of said delay line to said ground reference via a terminating impedance.

5. In an apparatus for imaging a body which includes a pulser/receiver; a transducer, having a number of segments, for transmitting ultrasound energy into said body and for converting ultrasound reflected from said body into electrical signals; and means coupled to said pulser/receiver for displaying an image of said body; a selectable focusing system comprising:
   a delay line having multiple fixed delay stages in a serially connected string;
   means for coupling said delay stages to respective ones of said segments; and
   switching means for coupling, under operator control, either one end of said delay line, or the other end of said delay line, or the common connection of said delay line, to said pulser/receiver.

6. The system as defined by claim 5 wherein said switching means is operative, when an end of said delay line is coupled to said pulser/receiver, to couple the other end of said delay line to a ground reference via a terminating impedance and to couple said common connection of said delay line to said ground reference, and said switching means is further operative, when said common connection of said delay line is coupled to said pulser/receiver, to couple both ends of said delay line to said ground reference via a terminating impedance.

7. A selectable delay system for coupling between a plurality of elements and an input/output terminal, the relative delays between the input/output terminal and the individual elements being selectable under operator control, comprising:
   a delay line having multiple fixed delay stages in a serially connected string;
   means for coupling said delay stages to respective ones of said elements;
   first and second impedances; and
   a switch having first, second, and third three-position sections under common control;
   the wipers of the first and third sections being coupled to opposite ends of said delay line, and the wiper of the second section being coupled to the common connection of said delay line;
   a first position of the first section, a second position of the second section, and a third position of the third section being coupled to said input/output terminal;
   a first and a third position of the second section being coupled to a ground reference;
   a second position of the first section and a second position of the third section being coupled via the first impedance to said common connection of said delay line;
   a third position of the first section and a first position of the third section being coupled via said second impedance to said ground reference.

8. In an apparatus for imaging a body which includes a pulser/receiver; a transducer, having a number of segments, for transmitting ultrasound energy into said body and for converting ultrasound reflected from said body into electrical signals; and means coupled to said pulser/receiver for displaying an image of said body; a selectable focusing system comprising:
   a delay line having multiple fixed delay stages in a serially connected string;
   means for coupling said delay stages to respective ones of said segments;
   first and second impedances; and
   a switch having first, second, and third three-position sections under common control;
   the wipers of the first and third sections being coupled to opposite ends of said delay line, and the wiper of the second section being coupled to the common connection of said delay line;

a first position of the first section, a second position of the second section, and a third position of the third section being coupled to said pulser/receiver;

a first and a third position of the second section being coupled to a ground reference;

a second position of the first section and a second position of the third section being coupled via the first impedance to said common connection of said delay line;

a third position of the first section and a first position of the third section being coupled via said second impedance to said ground reference.

* * * * *